US005543423A

United States Patent [19]
Zelle et al.

[11] Patent Number: 5,543,423
[45] Date of Patent: Aug. 6, 1996

[54] AMINO ACID DERIVATIVES WITH IMPROVED MULTI-DRUG RESISTANCE ACTIVITY

[75] Inventors: Robert E. Zelle, Stow; Matthew W. Harding, Acton, both of Mass.

[73] Assignee: Vertex Pharmaceuticals, Incorporated, Cambridge, Mass.

[21] Appl. No.: 377,285

[22] Filed: Jan. 23, 1995

Related U.S. Application Data

[63] Continuation-in-part of Ser. No. 340,830, Nov. 16, 1994.
[51] Int. Cl.$^6$ ............... A61K 31/44; C07D 211/32; C07D 213/46
[52] U.S. Cl. ............... 514/332; 514/885; 560/41; 560/169; 562/450; 562/561; 546/146; 546/147; 546/174; 546/175; 546/267; 546/335; 546/336; 546/337; 548/338.1; 548/470; 548/516; 564/153; 564/157
[58] Field of Search ............... 514/332, 885; 560/41, 169; 562/450, 561; 546/146, 147, 174, 175, 255, 267, 335, 336, 337; 548/338.1, 470, 576; 564/153, 157

[56] References Cited

U.S. PATENT DOCUMENTS

| | | | |
|---|---|---|---|
| 4,296,113 | 10/1981 | Ondetti et al. | 514/423 |
| 4,376,124 | 3/1983 | Carlson et al. | 514/532 |
| 4,579,840 | 4/1986 | Hahn | 514/14 |
| 4,920,218 | 4/1990 | Askin et al. | 540/456 |
| 5,135,915 | 8/1992 | Czarniecki et al. | 514/21 |
| 5,192,773 | 3/1993 | Armistead et al. | 514/315 |
| 5,330,993 | 7/1994 | Armistead et al. | 514/330 |

FOREIGN PATENT DOCUMENTS

| | | |
|---|---|---|
| 0172458 | 2/1986 | European Pat. Off. |
| 0196841 | 10/1986 | European Pat. Off. |
| 0384341 | 8/1990 | European Pat. Off. |
| 0457163 | 11/1991 | European Pat. Off. |
| 0515071 | 11/1992 | European Pat. Off. |
| 2328391 | 1/1994 | Germany. |
| 2247456 | 3/1992 | United Kingdom. |

OTHER PUBLICATIONS

D. R. Bender et al., "Periodate Oxidation of α-Ketoγ-Lactams. Enol Oxidation and β-Lactam Formation. Mechanism of Periodate Hydroxylation Reactions", *J. Org. Chem.*, 43(17), pp. 3354–3361 (1978).

G. Blaschke et al., "Investigation of Chromatographic Resolutions of Racemates, VI. Polymeric Amino Acid Derivatives As Optically Active Adsorbents", *Chem. Ber.*, 109(6), pp. 1967–1975 (1976).

D. Boesch et al., "In Vivo Circumvention of P–Glycoprotein–Mediated Multidrug Resistance of Tumor Cells with SDZ PSC 833", *Cancer Res.*, 51, pp. 4226–4233 (1991).

A. Boulmedais et al., "Stereochemistry of Electrochemical Reduction of Optically Active Alfa–Ketoamides. II. Electro–Reduction of Benzoylformamides Derived from S–(–)–Proline", *Bull. Soc. Chim. Fr.*, 2, pp. 189–191 (1989).

R. E. A. Callens et al., "Preparation of Trans–5–Hydroxy–L–Pipecolic Acid from L–Baikiain (1,2,5,6,-L–Tetrahydropyridine–2–Carboxylic Acid)", *Bull. Soc. Chim. Belg.*, 91, pp. 713–723 (1982).

S. P. C. Cole et al., "Overexpression of a Transporter Gene in a Multidrug Resistant Human Lung Cancer Cell Line", *Science*, 258, pp. 1650–1654 (1992).

R. S. Coleman et al., "Degradation and Manipulations of the Immunosuppressant FK506: Preparation of Potential Sythetic Intermediates", *Heterocycles*, 28, pp. 157–161 (1989).

F. Effenberger et al., "Amino Acids. 14. Diastereoselective Addition of Benzenesulfenyl Chloride to 1–Acyloylproline Esters", *Chem. Ber.*, 122(3), pp. 545–551 (1989).

M. Egbertson and S. J. Danishefsky, "Synthetic Route to the Tricarbonyl Region of FK–506", *J. Org. Chem.*, 54, pp. 11–12 (1989).

R. F. Epand and R. M. Epand, "The New Potent Immunosuppressant FK–506 Reverses Multidrug Resistance in Chinese Hamster Ovary Cells", *Anti–Cancer Drug Design 6*, Ap p. 189–193 (1991).

R. W. Finberg et al., "Prevention of HIV–1 Infection and Preservation of CD4 Function by the Binding of CPFs to gp120", *Science*, 249, pp. 287–291 (1990).

M. T. Goulet and J. Boger, "Degradative Studies on the Tricarbonyl Containing Macrolide Rapamycin", *Tetrahedron Lett.*, 31, pp. 4845–4848 (1990).

W. N. Hait and D. T. Aftab, "Rational Design and Pre–Clinical Pharmacology of Drugs for Reversing Multidrug Resistance", *Biochem. Pharmacol.*, 43, pp. 103–107 (1992).

W. N. Hait et al., "Activity of Cyclosporin A and a Non–Immunosuppressive Cyclosporin Against Multidrug Resistant Leukemic Cell Lines", *Cancer Commun.*, 1(1), pp. 35–43 (1989).

M. W. Harding et al., "A Receptor for the Immunosuppressant FK–506 is a Cis–Trans Peptidyl–Prolyl Isomerase", *Nature*, 341, pp. 758–760 (1989).

J. R. Hauske et al., "Investigation of the Effects of Synthetic, Non–Cytotoxic Immunophilin Inhibitors of MDR", *Bioorg. & Med. Chem. Lett.*, 4, pp. 2097–2102 (Sep. 8, 1994).

X. F. Hu et al., "Combined Use of Cyclosporin A and Verapamil in Modulating Multidrug Resistance in Human Leukemia Cell Lines", *Cancer Res.*, 50, pp. 2953–2957 (1990).

(List continued on next page.)

*Primary Examiner*—Shelley A. Dodson
*Attorney, Agent, or Firm*—James F. Haley, Jr.; Leslie A. McDonell; Andrew S. Marks

[57] ABSTRACT

The present invention relates to compounds that can maintain, increase, or restore sensitivity of cells to therapeutic or prophylactic agents. This invention also relates to pharmaceutical compositions comprising these compounds. The compounds and pharmaceutical compositions of this invention are particularly well-suited for treatment of multi-drug resistant cells, for prevention of the development of multi-drug resistance, and for use in multi-drug resistant cancer therapy.

17 Claims, No Drawings

OTHER PUBLICATIONS

G. Jedlitschky et al., "ATP–Dependent Transport of Glutathione S–Conjugates by the Multidrug Resistance–Associated Protein", *Cancer Res.*, 54, 4833–4836 (1994).

B. U. Kaczmar et al., "Snake–Cage Polymers, 1. Synthesis of Various Snake–Cage Polyelectrolytes Consisting of Polyacrylamides and an Anion Exchanger", *Makromol. Chem.*, 177(7), pp. 1981–1989 (1976).

N. Kartner and V. Ling; "Multidrug Resistance in Cancer", *Science*, pp. 110–117 (1989).

T. Kino et al., "FK–506, A Novel Immunosuppressant Isolated From a Streptomyces. II. Immunosuppressive Effect of FK–506 in Vitro", *J. Antibiot.*, 15, pp. 1256–1265 (1987).

N. Krishnamachhary et al., "The MRP Gene Associated with a Non–P–Glycoprotein Multidrug Resistance Encodes a 190–kDa Membrane Bound Gylcoportein", *Cancer Res.*, 53, 3658–3661 (1993).

I. Leier et al., "The MRP Gene Encodes an ATP–Dependent Export Pump for Leukotriene $C_4$ and Structurally Related Conjugates", *J. Biol. Chem.*, 269, pp. 27807–27810 (1994).

A. F. List et al., "Phase I/II Trial of Cyclosporine as a Chemotherapy–Resistance Modifier in Acute Leukemia", *J. Clin. Onc.*, 11, pp. 1652–1660 (1993).

E. Schneider et al., "Multidrug Resistance–Associated Protein Gene Overexpression and Reduced Drug Sensitivity of Topoisomerase II in a Human Breast Carcinoma MCF7 Cell Line Selected for Etopside Resistance", *Cancer Res.*, 54, pp. 152–158 (1994).

L. M. Slater et al., "Cyclosporin A Corrects Daunorubicin Resistance in Ehrlich Ascites Carcinoma", *Br. J. Cancer*, 54, pp. 235–238 (1986).

K. Soai et al., "Diastereoselective Reduction of Chiral Alpha–Ketoamides Derived from (S)–Proline Esters with Sodium Borohydride. Preparation of Optically Active Alpha–Hydroxy Acids", *J. Chem. Soc., Perkins Trans.*, 4, pp. 769–772 (1985).

K. Soai et al., "Asymmetric Allylation of $\alpha$–Keto Amides Derived from (S)–Proline Esters", *Peptide Chemistry 1986, Proceedings of the 24th Symposium on Peptide Chemistry*, (T. Miyazawa, Ed., Protein Research Foundation) pp. 327–330 (1987).

P. Sonneveld et al., "Clinical Modulation of Multidrug Resistance in Multiple Myeloma: Effect of Cyclosporine on Resistant Tumor Cells", *J. Clin. Onc.*, 12, pp. 1584–1591 (Aug. 1994).

H. Tanaka et al., "Structure of FK506: A Novel Immunosuppressant Isolated from Streptomyces", *J. Am. Chem. Soc.*, 109, pp. 5031–5033 (1987).

Z. Tokuza et al., "Studies on Tomaymycin. III. Syntheses and Antitumor Activity of Tomaymycin Analogs", *J. Antibiotics*, 26, pp. 1699–1708 (1983).

P. R. Twentyman, "Cyclosporins as Drug Resistance Modifiers", *Biochem. Pharmacol*, 43, pp. 109–117 (1992).

P. R. Twentyman et al., "Cyclosporin A and Its Analogues as Modifiers of Adriamycin and Vincristine Resistance in a Multi–drug Resistant Human Lung Cancer Cell Line", *Br. J. Cancer*, 56, pp. 55–57 (1987).

I. C. West, "What Determines the Substrate Specificity of the Multi–Drug–Resistance Pump?", *TIBS*, 15, pp. 42–46 (1990).

N. Yoshimura et al., "Effect of a New Immunosuppressive Agent, FK–506, on Human Lymphocyte Responses In Vitro", *Transplant.*, 47, pp. 356–359 (1989).

AMINO ACID DERIVATIVES WITH IMPROVED MULTI-DRUG RESISTANCE ACTIVITY

CROSS-REFERENCE TO PRIOR APPLICATION

This application is a continuation-in-part of copending application Ser. No. 340,830, filed Nov. 16, 1994.

TECHNICAL FIELD OF THE INVENTION

The present invention relates to novel compounds which can maintain, increase, or restore sensitivity of cells to therapeutic or prophylactic agents. This invention also relates to pharmaceutical compositions comprising these compounds. The compounds and pharmaceutical compositions of this invention are particularly well-suited for treatment of multi-drug resistant cells, for prevention of the development of multi-drug resistance and for use in multi-drug resistant cancer therapy.

BACKGROUND OF THE INVENTION

A major problem affecting the efficacy of chemotherapy regimens is the evolution of cells which, upon exposure to a chemotherapeutic drug, become resistant to a multitude of structurally unrelated drugs and therapeutic agents. The appearance of such multi-drug resistance often occurs in the presence of overexpression of a 170-kDA membrane P-glycoprotein (gp-170). The gp-170 protein is present in the plasma membranes of some healthy tissues, in addition to cancer cell lines, and is homologous to bacterial transport proteins (Hait et al., *Cancer Communications*, Vol. 1(1), 35 (1989); West, TIBS, Vol. 15, 42 (1990)). The protein acts as an export pump, conferring drug resistance through active extrusion of toxic chemicals. Although the mechanism for the pump is unknown, it is speculated that the gp-170 protein functions by expelling substances that share certain chemical or physical characteristics, such as hydrophobicity, the presence of carbonyl groups, or the existence of a glutathione conjugate (see West).

Recently, another protein responsible for multidrug resistance, MRP (multidrug resistance associated protein), was identified in H69AR cells, an MDR cell line that lacks detectable P-glycoprotein [S. P. C. Cole et al., *Science*, 258, pp. 1650–54 (1992)]. MRP has also been detected in other non-P-glycoprtoein MDR cell lines, such as HL60/ADR and MCF-7 brast carcinoma cells [(E. Schneider et al., *Cancer Res.*, 54, pp. 152–58 (1994); and N. Krishnamachary et al., *Cancer Res.*, 53, pp. 3658–61 (1993)].

The MRP gene encodes a 190 kD membrane-associated protein that is another member of the ATP binding cassette superfamily. MRP appears to function in the same manner as P-glycoprotein, acting as a pump for removing natural product drugs from the cell. A possible physiological function for MRP maybe ATP-dependent transport of glutathione S-conjugates [G. Jedlitschky et al., *Cancer RES.*, 54, pp. 4833–36 (1994); I. Leier et al., *J. Biol. Chem.*, 269, pp. 27807–10 (1994); and Muller et al., *Proc. Natl. Acad. Sci. USA*, 91, pp. 13033–37 (1994)].

The role of MRP in clinical drug resistance remains to be clearly defined, but it appears likely that MRP may be another protein responsible for a broad resistance to anti-cancer drugs.

Various chemical agents have been administered to repress multi-drug resistance and restore drug sensitivity. While some drugs have improved the responsiveness of multi-drug resistant ("MDR") cells to chemotherapeutic agents, they have often been accompanied by undesirable clinical side effects (see Hait et al.). For example, although cyclosporin A ("CsA"), a widely accepted immunosuppressant, can sensitize certain carcinoma cells to chemotherapeutic agents (Slater et al., *Br. J. Cancer*, Vol. 54, 235 (1986)), the concentrations needed to achieve that effect produce significant immunosuppression in patients whose immune systems are already compromised by chemotherapy (see Hait et al.). In addition, CsA usage is often accompanied by adverse side effects including nephrotoxicity, hepatotoxicity and central nervous system disorders. Similarly, calcium transport blockers and calmodulin inhibitors both sensitize MDR cells, but each produces undesirable physiological effects (see Hait et al.; Twentyman et al., *Br. J. Cancer*, Vol. 56, 55 (1987)).

Recent developments have led to agents said to be of potentially greater clinical value in the sensitization of MDR cells. These agents include analogs of CsA which do not exert an immunosuppressive effect, such as 11-methyl-leucine cyclosporin (11-met-leu CsA) (see Hair et al.; Twentyman et al.), or agents that may be effective at low doses, such as the immunosuppressant FK-506 (Epand and Epand, *Anti-Cancer Drug Design* 6, 189 (1991)). PCT publication WO 94/07858 refers to a novel class of MDR modifying agents with some structural similarities to the immunosuppressants FK-506 and rapamycin. Despite these developments, there is still a need for more effective agents which may be used to resensitize MDR cells to therapeutic or prophylactic agents or to prevent the development of multi-drug resistance.

SUMMARY OF THE INVENTION

The present invention provides novel compounds that have a surprisingly improved ability, as compared with previously described MDR modifiers, to maintain, increase or restore drug sensitivity in multi-drug resistant ("MDR") cells, compositions containing these compounds and methods for using them. The compounds of this invention may be used alone or in combination with other therapeutic or prophylactic agents to maintain, increase or restore the therapeutic or prophylactic effects of drugs in cells, especially MDR cells, or to prevent the development of MDR cells. According to one embodiment of this invention, these novel compounds, compositions and methods are advantageously used to aid or enhance chemotherapy regimens for the treatment or prophylaxis of cancer and other diseases.

The present invention also provides methods for preparing the compounds of this invention and intermediates useful in those methods.

DETAILED DESCRIPTION OF THE INVENTION

This invention relates to a novel class of compounds represented by formula (I):

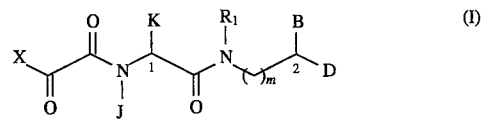

wherein $R_1$, B and D are independently:

Ar, (C1–C6)-straight or branched alkyl, (C2–C6)-straight or branched alkenyl or alkynyl, (C5–C7)-cycloalkyl-substituted (C1–C6)-straight or branched alkyl, (C5–C7)-cycloalkyl-substituted (C3–C6)-straight or branched alkenyl or alkynyl, (C5–C7)-cycloalkenyl-substituted (C1–C6)-straight or branched alkyl, (C5–C7)-cycloalkenyl-substituted (C3–C6)-straight or branched alkenyl or alkynyl, Ar-substituted (C1–C6)-straight or branched alkyl, Ar-substituted (C3–C6)-straight or branched alkenyl or alkynyl;

wherein any one of the $CH_2$ groups of said alkyl chains may be optionally replaced by a heteroatom selected from the group consisting of O, S, SO, $SO_2$, and NR, wherein R is selected from the group consisting of hydrogen, (C1–C4)-straight or branched alkyl, (C3–C4)-straight or branched alkenyl or alkynyl, and (C1–C4) bridging alkyl wherein a bridge is formed between the nitrogen and a carbon atom of said heteroatom-containing chain to form a ring, and wherein said ring is optionally fused to an Ar group;

B and D may also be hydrogen;

J is selected from the group consisting of (C1–C6)-straight or branched alkyl, (C3–C6)-straight or branched alkenyl, Ar-substituted (C1–C6)-straight or branched alkyl, and Ar-substituted (C3–C6)-straight or branched alkenyl or alkynyl;

K is selected from the group consisting of (C1–C6)-straight or branched alkyl, Ar-substituted (C1–C6)-straight or branched alkyl, Ar-substituted (C2–C6)-straight or branched alkenyl or alkynyl, and cyclohexylmethyl;

X is selected from the group consisting of Ar, $-OR_2$, and $-NR_3R_4$;

wherein $R_2$ has the same definition as $R_1$; and $R_3$ and $R_4$ independently have the same definitions as B and D, or $R_3$ and $R_4$ are taken together to form a 5–7 membered heterocyclic aliphatic or aromatic ring;

wherein Ar is a carbocyclic aromatic group selected from the group consisting of phenyl, 1-naphthyl, 2-naphthyl, indenyl, azulenyl, fluorenyl, and anthracenyl;

or Ar is a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar may contain one or more substituents which are independently selected from the group consisting of hydrogen, halogen, hydroxyl, nitro, $-SO_3H$, trifluoromethyl, trifluoromethoxy, (C1–C6)-straight or branched alkyl, (C2–C6)-straight or branched alkenyl, O-[(C1–C6)-straight or branched alkyl, O-(C3–C4)-straight or branched alkenyl, O-benzyl, O-phenyl, 1,2-methylenedioxy, $-NR_5R_6$, carboxyl, N-(C1–C5-straight or branched alkyl or C3–C5-straight or branched alkenyl) carboxamides, N,N-di-(C1–C5-straight or branched alkyl or C3–C5-straight or branched alkenyl) carboxamides, morpholinyl, piperidinyl, O—M, $CH_2-(CH_2)_q$—M, O—$(CH_2)_q$—M, $(CH_2)_q$—O—M, and CH=CH—M;

wherein $R_5$ and $R_6$ are independently selected from the group consisting of hydrogen, (C1–C6)-straight or branched alkyl, (C3–C6)-straight or branched alkenyl or alkynyl and benzyl; M is selected from the group consisting of 4-methoxyphenyl, 2-pyridyl, 3-pyridyl, 4-pyridyl, pyrazyl, quinolyl, 3,5-dimethylisoxazoyl, 2-methylthiazoyl, thiazoyl, 2-thienyl, 3-thienyl and pyrimidyl; and q is 0–2; and m is 0 or 1.

Preferably, at least one of B or D is independently represented by the formula $-(CH_2)_r-(Z)-(CH_2)_s-Ar$, wherein:

r is 1–4;

s is 0–1;

Ar is as defined above for compounds of formula (I); and each Z is independently selected from the group consisting of $CH_2$, O, S, SO, $SO_2$, and NR, wherein R is selected from the group consisting of hydrogen, (C1–C4)-straight or branched alkyl, (C3–C4)-straight or branched alkenyl or alkynyl, and (C1–C4) bridging alkyl, wherein a bridge is formed between the nitrogen atom and the Ar group.

The preferred Ar groups of this invention include phenyl, 2-pyridyl, 3-pyridyl, 4-pyridyl, imidazolyl, indolyl, isoindolyl, quinolinyl, isoquinolinyl, 1,2,3,4-tetrahydroisoquinolinyl, and 1,2,3,4-tetrahydroquinolinyl, wherein said Ar may contain one or more substituents which are independently selected from the group consisting of hydrogen, hydroxyl, nitro, trifluoromethyl, (C1–C6)-straight or branched alkyl, O-[(C1–C6)-straight or branched alkyl], halogen, $SO_3H$, and $NR_3R_4$, wherein $R_3$ and $R_4$ are independently selected from the group consisting of (C1–C6)-straight or branched alkyl, (C3–C6)-straight or branched alkenyl, hydrogen and benzyl; or wherein $R_3$ and $R_4$ can be taken together to form a 5–6 membered heterocyclic ring.

Examples of some preferred compounds of formula (I) have the formula (II) or (III):

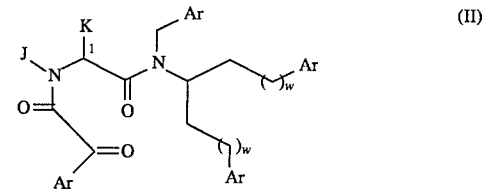

(II)

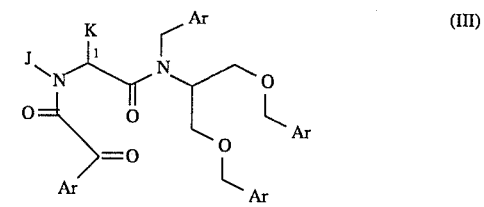

(III)

wherein J and K are independently (C1–C6)-straight or branched alkyl or Ar-substituted (C1–C6)-straight or -branched alkyl; each Ar is independently one of the preferred aryl groups of this invention, as defined above; and each w is 1 or 2.

Table I provides some examples of preferred compounds of formula (I), wherein X is a 3,4,5-trimethoxyphenyl group, and m is 0 (formula (I')) wherein for each compound, B, D, J, K, and $R_1$ are defined as indicated.

TABLE 1

(I')

| Cpd. | B* | D* | J | K | R₁ |
|---|---|---|---|---|---|
| 6 | 4-Pyr—(CH₂)₂— | 4-Pyr—(CH₂)₂— | CH₃ | PhCH₂ | 4-F—PhCH₂— |
| 7 | 4-Pyr—(CH₂)₂— | 4-Pyr—(CH₂)₂— | CH₃ | PhCH₂ | PhCH₂— |
| 8 | 4-Pyr—(CH₂)₂— | 4-Pyr—(CH₂)₂— | CH₃ | PhCH₂ | 4-Cl—PhCH₂— |
| 9 | 4-Pyr—(CH₂)₂— | 4-Pyr—(CH₂)₂— | CH₃ | 4-Cl—PhCH₂ | PhCH₂— |
| 10 | H— | PH(CH₂)₃ | CH₃ | PhCH₂ | 4-Pyr-CH₂ |
| 12 | 3-Pyr—(CH₂)₃— | 3-Pyr—(CH₂)₃— | CH₃ | PhCH₂ | PhCH₂— |
| 14 | 4-Pyr—(CH₂)₂— | 4-Pyr—(CH₂)₂— | CH₃ | PhCH₂ | CH₃ |
| 15 | 3-Pyr—(CH₂)₃— | 3-Pyr—(CH₂)₃— | CH₃ | PhCH₂ | CH₃ |
| 16 | 4-Pyr—(CH₂)₂— | 4-Pyr—(CH₂)₂— | CH₃ | (CH₃)₂CHCH₂— | PhCH₂— |
| 17 | 4-Pyr—(CH₂)₂— | 4-Pyr—(CH₂)₂— | CH₃ | (CH₃)₂CHCH₂— | 4-F—PhCH₂— |
| 18 | 4-Pyr—(CH₂)₂— | 4-Pyr—(CH₂)₂— | CH₃ | (CH₃)₂CHCH₂— | 4-Cl—PhCH₂— |
| 19 | 4-Pyr—(CH₂)₂— | 4-Pyr—(CH₂)₂— | CH₃ | 4-Cl—PhCH₂ | 4-F—PhCH₂— |
| 21 | H— | 3-Im-(CH₂)₂ | CH₃ | PhCH₂ | PhCH₂— |
| 23 | Ph(CH₂)₂— | Ph(CH₂)₂— | CH₃ | PhCH₂ | 1H—Im—CH₂ |

Another embodiment of this invention is directed to compounds of formula (XXXI):

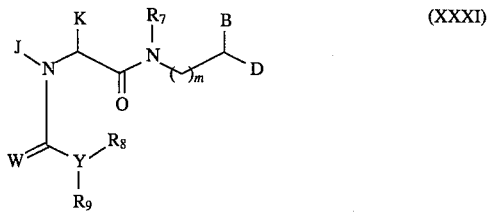

(XXXI)

wherein m, B, D, J and K are as defined above for compounds of formula (I);

$R_7$ has the same definition as $R_1$ as defined above for compounds of formula (I);

W is O or S;

Y is O or N, wherein when Y is O, then $R_8$ is a lone pair (as used herein, the term "lone pair" refers to a lone pair of electrons, such as the lone pair of electrons present on divalent oxygen) and $R_9$ is selected from the group consisting of Ar, (C1–C6)-straight or branched alkyl, and (C3–C6)-straight or branched alkenyl or alkynyl; and when Y is N, then $R_8$ and $R_9$ are independently selected from the group consisting of Ar, (C1–C6)-straight or branched alkyl, and (C3–C6)-straight or branched alkenyl or alkynyl; or $R_8$ and $R_9$ are taken together to form a heterocyclic 5–6 membered ring selected from the group consisting of pyrrolidine, imidazolidine, pyrazolidine, piperidine, and piperazine;

wherein the term Ar is as defined above for compounds of formula (I).

Preferably W in compounds of formula (XXXI) is oxygen. Also preferred are compounds of formula (XXXI) wherein at least one of B or D is independently represented by the formula —(CH₂)$_r$—(Z)—(CH₂)$_s$—Ar, wherein:

r is 1–4;

s is 0–1; and each Z is independently selected from the group consisting of $CH_2$, O, S, SO, $SO_2$, and NR, wherein R is selected from the group consisting of hydrogen, (C1–C4)-straight or branched alkyl, (C3–C4)-straight or branched alkenyl or alkynyl, and (C1–C4) bridging alkyl, wherein a bridge is formed between the nitrogen atom and the Ar group.

As defined herein, the compounds of this invention include all optical and racemic isomers.

As defined herein, all compounds of this invention include pharmaceutically acceptable derivatives thereof. A "pharmaceutically acceptable derivative" denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to maintain, increase or restore sensitivity of MDR cells to therapeutic or prophylactic agents or to prevent development of multi-drug resistance.

Compounds of this invention, represented by formulae (I) and (I'), may be obtained using any conventional technique. Preferably, these compounds are chemically synthesized from readily available starting materials, such as alpha-amino acids. Modular and convergent methods for the synthesis of these compounds are also preferred. In a convergent approach, for example, large sections of the final product are brought together in the last stages of the synthesis, rather than by incremental addition of small pieces to a growing molecular chain.

Scheme 1 illustrates a representative example of a convergent process for the synthesis of compounds of formula (I) (wherein m is 0 or 1). The process comprises coupling of a protected amino acid of formula (IV), wherein P is a protecting group, with an amine of formula (V) to provide an amino amide of formula (VI). Protected alpha-amino acids are well known in the art and many are commercially available. For example, common protecting groups and convenient methods for the protection of amino acids are described in T. W. Greene, P. G. M. Wuts, *Protective Groups in Organic Chemistry*, 2nd Ed., John Wiley and Sons, New York (1991). Alkoxycarbonyl groups are preferred for protection of the nitrogen atom in compounds of formula (IV), with t-butoxycarbonyl (Boc), benzyloxycarbonyl (Cbz), allyloxycarbonyl (Alloc), and trimethylsilylethoxycarbonyl (Teoc) being more preferred.

After the coupling, compounds of formula (VI) are deprotected under suitable deprotection conditions (see Greene, supra), and the free amino group of (VII) is then acylated using a preformed acyl chloride of formula (VIII') or any other activated form of a compound of formula (VIII). The halogen chloro group in (VIII') may be replaced with other leaving groups or activating groups known in the art such as other halogens, imidazolyl or pentafluorophenoxy groups.

Amines of formula (V) wherein m is 0 (formula (V')) can also be conveniently prepared, for example, as illustrated in Schemes 2, 3 and 4. Reaction of an organometallic reagent of formula (XV) and a carboxylic acid of formula (XVI), or an equivalent (e.g., the Weinreb amide), provides ketones of formula (XVII).

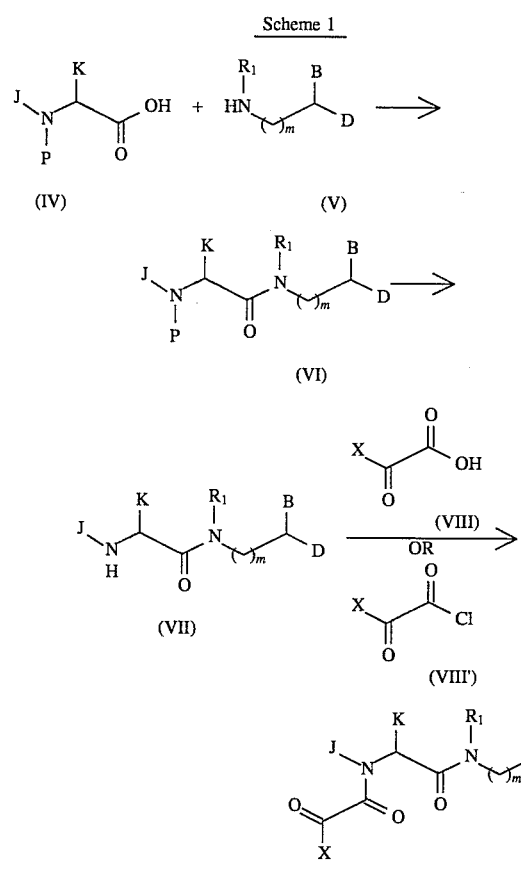

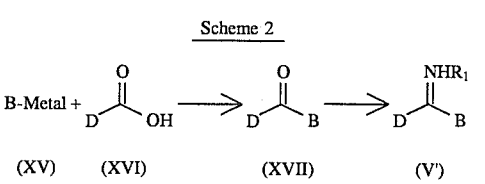

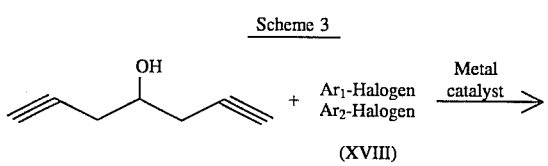

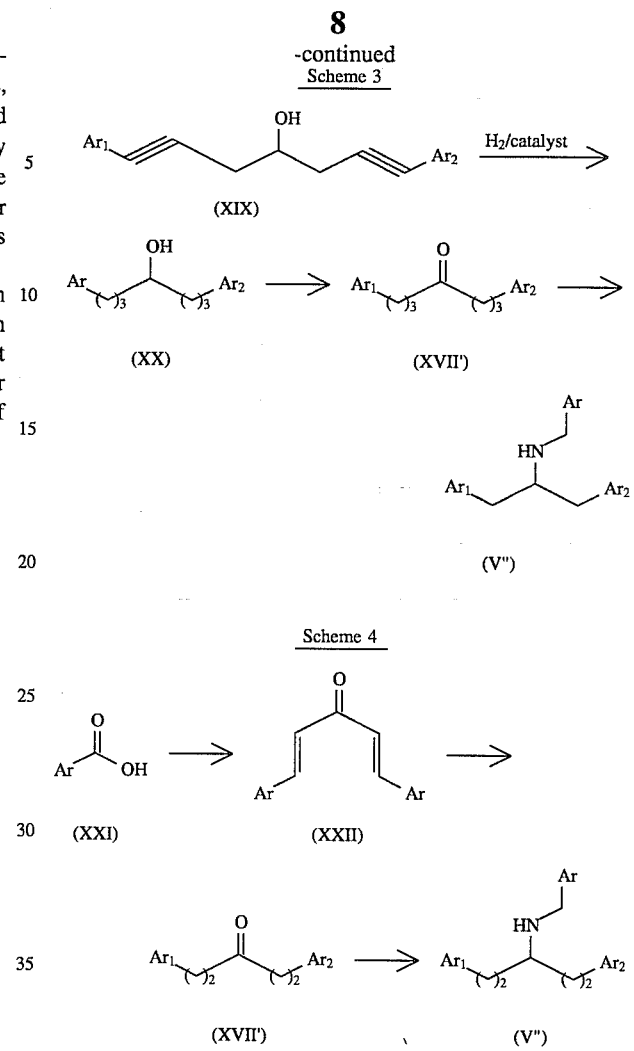

Such ketones can be readily converted to amines of formula (V') using any of the well known procedures in the art, for example, through reductive amination (Scheme 2).

Alternatively (Scheme 3), 1,6-heptadiyn-4-ol can be coupled via a metal-catalyzed reaction to aromatic halides of formula (XVIII) to give an alcohol of formula (XIX). Subsequent hydrogenation provides an alcohol of formula (XX). Oxidation to a ketone of formula (XVII') and subsequent amination would then provide the desired amine of formula (V").

In yet another embodiment of the processes of this invention (Scheme 4), a ketodiene of formula (XXII), derived from an aldehyde of formula (XXI), is reduced to yield a ketone of formula (XVII"). Again, a standard amination reaction provides the amine of formula (V''').

Thus, this invention also provides a method for preparing compounds of formula (I) comprising the steps of:

(a) coupling an amino acid of formula (IV) with an amine of formula (V) to give an amide of formula (VI);

(b) deprotecting the amide of formula (VI) to give an amino amide of formula (VII); and (c) acylating the amino amide of formula (VII) with a compound of formula (VIII):

It should be appreciated by those of ordinary skill in the art that a large variety of compounds of formula (I) may be readily prepared, according to the processes illustrated in synthetic Schemes 1–4. The same processes may be used for the synthesis of many different end-products, by altering the variables in the starting materials.

Optically active compounds of formula (I) may also be prepared using optically active starting materials, thus obviating the need for resolution of enantiomers or separation of diastereomers at a late stage in the synthesis.

Scheme 5 illustrates a representative example of a process for the preparation of a preferred subclass of compounds of formula (XXXI) wherein W is an oxygen. As shown in Scheme 5, ureas and carbamates of formula (XXXI') are prepared in a manner analogous to the processes for preparation of compounds of formula (I) depicted in Scheme 1. Thus, a protected amino acid of formula (IV) can be coupled to a secondary amine of formula ($V^{iv}$). Deprotection followed by acylation with an acid chloride of formula (XXX) would then provide the desired compound of formula (XXXI').

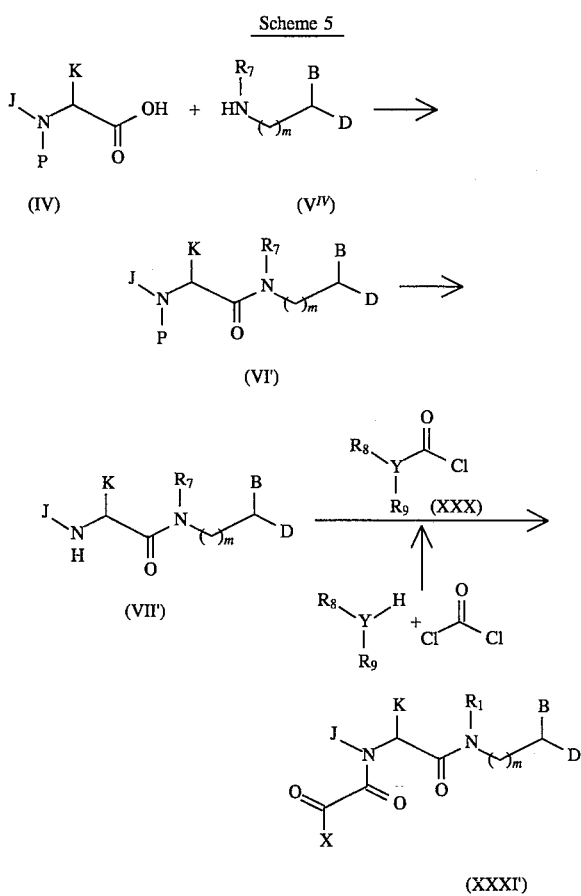

Scheme 5

It will also be appreciated by those of ordinary skill in the art that the above synthetic schemes are not intended to comprise a comprehensive list of all means by which the compounds or the intermediates of this invention may be synthesized. Further methods or modifications of the above general schemes will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of this invention are characterized by the ability to increase, restore or maintain the sensitivity of MDR cells to cytotoxic compounds, such as, for example, those typically used in chemotherapy. Based on that ability, the compounds of this invention are advantageously used as chemosensitizing agents, to increase the effectiveness of chemotherapy in individuals who are afflicted with drug-resistant cancers, tumors, metastases or disease. In addition, the compounds of this invention are capable of maintaining sensitivity to therapeutic or prophylactic agents in non-resistant cells. Therefore, the compounds of this invention are useful in treating or preventing multi-drug resistance ("MDR") in a patient. More specifically, these compounds are useful in treating of preventing P-glycoprotein-meidated MDR and MRP-mediated MDR.

As used throughout this application, the term "patient" refers to mammals, including humans. And the term "cell" refers to mammalian cells, including human cells.

As used herein, the terms "sensitizing agent", "sensitizer", "chemosensitizing agent", "chemosensitizer" and "MDR modifier" denote a compound having the ability to increase or restore the sensitivity of an MDR cell, or to maintain the sensitivity of a non-resistant cell, to one or more therapeutic or prophylactic agents. The term "MDR sensitization" and "sensitization" and "resensitization" refer to the action of such a compound in maintaining, increasing, or restoring drug sensitivity.

The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term "parenteral" as used herein includes subcutaneous, intravenous, intramuscular, intra-articular, intrasynovial, intrasternal, intrathecal, intrahepatic, intralesional and intracranial injection or infusion techniques.

The pharmaceutical compositions of this invention comprise any of the compounds of the present invention, or pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex and diet of the patient, the time of administration and rate of excretion of the compound, the particular drug combination, and the judgment of the treating physician and the severity of the particular disease being treated. The amount of active ingredient may also depend upon the therapeutic or prophylactic agent, if any, with which the ingredient is co-administered. The term "pharmaceutically effective amount" refers to an amount effective to prevent multi-drug resistance or to maintain, increase or restore drug sensitivity in MDR cells.

Dosage levels of between about 0.01 and about 100 mg/kg body weight per day, preferably between about 0.5 and about 50 mg/kg body weight per day of the active ingredient compound are useful. A typical preparation will contain between about 5% and about 95% active compound (w/w). Preferably, such preparations contain between about 20% and about 80% active compound.

When the compounds of this invention are administered in combination therapies with other agents, they may be administered sequentially or concurrently to the patient. Alternatively, pharmaceutical or prophylactic compositions according to this invention may comprise a combination of a compound of this invention and another therapeutic or prophylactic agent.

For example, the compounds may be administered either alone or in combination with one or more therapeutic agents, such as chemotherapeutic agents, (e.g., actinomycin D, doxorubicin, vincristine, vinblastine, etoposide, amsacrine, mitoxantrone, tenipaside; taxol and colchicine) and/or a chemosensitizing agent (e.g., cyclosporin A and analogs, phenothiazines and thioxantheres), in order to increase the susceptibility of the MDR cells within the patient to the agent or agents.

In order that this invention may be more fully understood, the following examples are set forth. These examples are for the purpose of illustration only and are not to be construed as limiting the scope of the invention in any way.

EXAMPLES

General Methods

Proton nuclear magnetic resonance ($^1$H NMR) spectra were recorded at 500 MHz on a Bruker AMX 500. Chemical shifts are reported in parts per million (δ) relative to Me4Si (δ0.0). Analytical high performance liquid chromatography was performed on either a Waters 600E or a Hewlett Packard 1050 liquid chromatograph.

Example 1

1,5-Di(pyridin-4-yl)-pent-1,4-dien-3-one (Compound 1): To a solution of 1,3-acetone dicarboxylic acid (21.0 g, 0.144 mmol) in absolute ethanol (200 mL) was added dropwise 4-pyridine carboxaldehyde (30.8 g, 0.288 mmol). Gas evolution occurred throughout the addition. After stirring at room temperature for 2 h, the reaction was treated with concentrated hydrochloric acid (100 mL) and heated to 80° C. at which time a yellow precipitate slowly formed. An additional 500 mL of ethanol was added to allow for stirring of the suspension. After 1 hr at 80° C., the precipitate was collected by filtration, washed with ethanol and dried under vacuum to provide the desired product as a yellow solid. The resulting dihydrochloride salt was recrystallized form methylene chloride to provide pure compound 1.

Example 2

1,5-Di(pyridin-4-yl)-pentan-3-one (Compound 2): To a slurry of Compound 1 (21.3 g, 67.4 mmol) in 1,4-dioxane (40 mL) was added triethylamine (48.1 mL, 0.346 mol), formic acid (6.54 mL, 0.145 mol) and 10% palladium on carbon (0.7 g) and the resulting mixture heated to reflux. After stirring at reflux for 1 hr, the reaction was cooled to room temperature filtered and concentrated in vacuo. The resulting residue was chromatographed over silica gel (elution with 5% methanol/methylene chloride) to provide the desired material.

Example 3

(4-Fluorobenzyl)-(3-(pyridin-4yl)-1-(2-(pyridin-4-y)-ethyl)propyl)amine (Compound 3): To a flask equipped with a Dean-Stark trap, was added compound 2 (12.46 g, 51.91 mmol), 4-fluorobenzylamine (5.93 mL, 51.91 mmol) and benzene (50 mL) and the resulting mixture was heated to reflux. After the collection of 930 μL of water, the reaction mixture was cooled and concentrated. The residue was taken up into ethanol (50 mL) and added to a slurry of sodium borohydride (2.96 g, 77.8 mmol) in ethanol (50 mL) and the mixture heated to 80° C. and stirred for 1 h. The reaction mixture was cooled and concentrated. The residue was taken up into water, acidified to pH 3.0 with 6N hydrochloric acid. The aqueous phase was washed with ethyl acetate (2X). The aqueous phase was made basic with sodium hydroxide to a pH of 10 and the product extracted with methylene chloride (2X). The organics were combined, washed with brine, dried over anhydrous magnesium sulfate, filtered and concentrated in vacuo. Chromatography of the residue over silica gel (elution with 5% methanol/methylene chloride) provided compound 3.

Example 4

(S)-N-(4-Fluorobenzyl)-2-(N-methyl-N-tert-butylcarbamoylyl)amino- 3-phenyl-N-(pyridin-4-yl)-1-(2-(pyridin-4-yl)-ethyl)propyl)propionamide (Compound 4): To a solution of compound 3 (550 mg, 1.66 mmol) and (L)-BOC-N-methyl-phenylalanine (700 mg, 2.5 mmol) in methylene chloride (4.0 mL) containing diisopropylethylamine (300 μL, 1.72 mmol) was added (3-dimethylaminopropyl)-3-ethyl-carbodiimide hydrochloride (480 mg, 2.5 mmol) and the reaction was allowed to stir for 48 h. The reaction was diluted with ethyl acetate and water. The layers were separated and the aqueous phase reextracted with ethyl acetate. The organics were combined, washed with saturated sodium bicarbonate, water and brine, dried over anhydrous magnesium sulfate, filtered and concentrated in vacuo. Chromatography of the residue over silica gel (elution with 5% methanol/methylene chloride) provided compound (4).

Example 5

(S)-N-(4-Fluorobenzyl)-2-methylamino-3-phenyl-N-(3-(pyridin-4 -yl)-1-(2-(pyridin-4-yl)-ethyl)propyl)propion amide (Compound 5): Compound 4 was dissolved in methylene chloride (10 mL) and treated with trifluoroacetic acid (4.0 mL). After stirring at room temperature for 1.5 h, the reaction was concentrated in vacuo. The residue was neutralized with saturated potassium carbonate and extracted with ethyl acetate (2x). The extracts were combined, washed with water, dried over anhydrous magnesium sulfate, filtered and concentrated in vacuo to provide Compound 5.

Example 6

(S)-N-(4-Fluorobenzyl)-2-(methyl-(2-oxo-2-(3,4,5-trimethoxyphenyl)acetyl)amino)-3-phenyl-N-(3 -(pyridin-4-yl)-1-(2-(pyridin-4-yl)-ethyl)propyl)propionamide (Compound 6): To a solution of compound 5 (500 mg, 0.98 mmol) and 3,4,5-trimethoxybenzyolformic acid (294 mg, 1.22 mmol) in methylene chloride (4.0 mL) containing N,N-dimethyl-formamide (0.4 mL) was added (3-dimethylaminopropyl)-3-ethylcarbodiimide hydrochloride (235 mg, 1.22 mmol) and the reaction was allowed to stir for 24 h. The reaction was diluted with ethyl acetate and water. The layers were separated and the aqueous phase reextracted with ethyl acetate. The organics were combined, washed with saturated sodium bicarbonate, water and brine, dried over anhydrous magnesium sulfate, filtered and concentrated in vacuo. The residue was chromatographed on silica gel (elution with 5% methanol/methylene chloride) to provide the desired product. $^1$H NMR as a mixture of rotomers (500 MHz, CDCl$_3$) δ8.48–8.44 (m), 8.38 (dd), 7.36–7.33 (m), 7.28–7.18 (m), 7.13–7.02 (m), 6.97–6.87 (m), 6.58 (d), 6.00 (dt), 5.81 (t), 4.97 (br, s), 4.81 (d), 4.23–4.16 (m), 3.93 (s), 3.90 (s), 3.85 (s), 3.76 (s), 3.59 (dd), 3.28 (dd), 3.20 (s), 3.15 (s), 3.04–2.96 (m), 3.02 (s), 3.01 (s), 2.94 (dd), 2.63 (dt), 2.53–2.37 (m), 1.92–1.78 (m), 1.72–1.62 (m), 1.52–1.42 (m).

Example 7

(S)-N-Benzyl-2-(methyl-(2-oxo-2-(3,4,5-trimethoxyphenyl)acetyl)amino)- 3-phenyl-N-(3-(pyridin-4-yl)-1-(2-pyridin-4-yl-ethyl)propyl)propionamide (Compound 7): Compound 7 was prepared according to the protocols of Examples 3-6, by replacing 4-fluorobenzylamine with benzylamine. $^1$H NMR as a mixture of rotomers (500 MHz, CDCl$_3$) δ8.48 (dd), 8.53 (dd), 8.43 (dd), 8.35 (dd), 7.38 (d), 7.30–7.18 (m), 7.17–7.02 (m), 6.93 (s), 6.89 (d), 6.54 (d), 6.03 (dd), 5.86 (t), 5.08 (br, d), 4.88 (d), 4.32–4.18 (m), 3.95 (s), 3.89 s), 3.86 (s), 3.73 (s), 3.63 (dd), 3.23–3.19 (m), 3.09 (dd), 3.05 (s), 3.03 (s), 2.97 (dd), 2.63 (dt), 2.57–2.37 (m), 2.24 (dt), 2.06 (m), 1.95–1.76 (m), 1.74–1.63 (m), 1.54–1.44 (m).

Example 8

(S)-N-(4-Chlorobenzyl)-2-(methyl-(2-oxo-2-(3,4,5-trimethoxyphenyl)acetyl)amino)-3-phenyl-N-( 3-(pyridin-4-yl)-1-(2-(pyridin-4-yl)-ethyl)propyl)propionamide (Compound 8): Compound 8 was prepared according to the protocols of Examples 3–6, by replacing 4-fluorobenzylamine with 4-chlorobenzylamine. $^1$H NMR as a mixture of rotomers (500 MHz, CDCl$_3$) δ8.49 (dt), 8.45 (dd), 8.40 (dd), 7.69 (d ), 7.31–7.14 (m), 7.12 (s), 7.08–7.03 (m), 6.98 (s), 6.94–6.91 (m), 6.85 (d), 6.02 (dd), 5.79 (t), 4.99 (br d), 4.83 (d), 4.22–4.16 (m), 3.96 (m), 3.91 (s), 3.88 (s), 3.87 (s), 3.81 (s), 3.78 (s), 3.61 (dd), 3.33 (dd ), 3.21 (s), 3.17 (s), 3.04 (s), 3.03 (s), 3.03–3.00 (m), 2.95 (dd), 2.65 (dt), 2.56–2.40 (m), 2.28 (dr), 1.90–1.80 (m), 1.75–1.66 (m), 1.52–1.43 (m).

Example 9

(S)-N-Benzyl-3-(4-chlorophenyl)-2-(methyl-(2-oxo-2-(3,4,5 -trimethoxyphenyl)acetyl)amino)-N-(3-(pyridin-4-yl)-1-(2-(pyridin-4-yl)-ethyl)propyl)propionamide (Compound 9): Compound 9 was prepared according to the protocols of Examples 3–6, by replacing 4-fluorobenzylamine with benzylamine and (L)-BOC-N-methylphenylalanine with (L)-BOC-N-methyl-4-chlorophenylalanine. $^1$H NMR as a mixture of rotomers (500 MHz, CDCl$_3$) δ8.48 (dd), 8.45 (dt), 8.38 (dd), 7.32–6.87 (m), 6.58 (d), 5.94 (dd), 5.78 (t), 5.05 (brd), 4.83 (d), 4.26 (dd), 4.15 (m), 3.97 (s), 3.89 (s), 3.86 (s), 3.75 (s), 3.57 (dd), 3.20(s), 3.15 (s), 3.15–3.09 (m), 3.05–2.96 (m), 3.01 (s), 3.00 (s), 2.91 (dd), 2.65–2.38 (m), 2.26 (dt), 1.94–1.47 (m).

Example 10

(S)-2-(Methyl-(2-oxo-2-(3,4,5-trimethoxyphenyl)acetyl)-amino)-3-phenyl-N-(4-phenylbutyl)-N-[(pyridin-4-yl)-methyl]propionamide (Compound 10 ): Compound 10 was prepared according to the protocols of Examples 3–6, by replacing 4-fluorobenzylamine with 4-phenylbutylamine and compound 2 with 4-pyridinecarboxaldehyde. $^1$H NMR as a mixture of rotomers (500 MHz, CDCl$_3$) δ8.46 (dd), 8.42 (dd), 7.30–7.23 (m), 7.18–7.11 (m), 7.11 (s), 7.10 (s), 6.90 (d), 6.77 (d), 5.88 (t), 5.60 (dd), 4.85 (d), 4.50 (d), 4.28 (d), 3.93 (s), 3.83 (s), 3.81 (s), 3.80 (s), 3.65–3.50 (m), 3.37 (m), 3.20–3.15 (m), 3.08–3.06 (m), 3.06 (s), 3.05 (s), 2.92 (dd), 2.60 (m), 2.54 (m), 1.60–1.48 (m), 1.38–1.28 (m).

Example 11

1,7-Di(pyridin-4-yl)-heptan-4-one (Compound 11): To a solution of 1,7-di(pyridin-4-yl)-heptan-4-ol (4.1 g, 15.2 mmol) in methylene chloride (50 mL) at 0° C., was added potassium bromide (180 mg) and 2,2,6,6-tetramethyl-1-piperidinyloxy, free radical (71 mg). To the resulting mixture was added dropwise a solution of sodium bicarbonate (510 mg) in sodium hypochlorite (65 ml). After the addition was complete, the reaction mixture was warmed to room temperature and stirred for 30 min. The mixture was diluted with ethyl acetate and water. The layers were separated and the aqueous layer reextracted with ethyl acetate. The organics were combined, washed with water and brine, dried over anhydrous magnesium sulfate, filtered and concentrated in vacuo. Chromatography of the residue over silica gel (elution with 5% methanol/methylene chloride) provided compound 11.

Example 12

(S)-N-Benzyl 2-(methyl-(2-oxo-2-(3,4,5-trimethoxyphenyl)acetyl)amino)-3-phenyl-N-(3-(pyridin-4 -yl)-1-(2-(pyridin-4-yl)-propyl)butyl)propionamide Compound 12 was prepared according to the protocols of Examples 3–6, by replacing 4-fluorobenzylamine with benzylamine and compound 2 with compound 11. $^1$H NMR as a mixture of rotometers (500 MHz, CDCl$_3$) δ8.43–8.38 (m), 8.30 (m), 8.16 (m), 7.53–7.45 (m) 7.34 (m), 7.32 (m), 7.26–7.22 (m), 7.19–7.07 (m), 7.00–6.83 (m), 5.89 (dd), 5.72 (t), 4.90 (d, 4.72 (d), 4.10 (d), 4.00 (d), 3.93 (s), 3.91 (s), 3.85 (s), 3.74 (s), 3.52 (dd), 3.16–3.10 (m), 3.04 (s), 2.99 (dd), 2.93 (s), 2.84 (dd), 2.67–2.38 (m), 2.30 (m), 2.2 (m), 1.63–1.12 (m), 0.94 (m).

Example 13

Methyl-(3-(pyridin-4-yl)-1-(pyridin-4-yl)-ethyl)propyl)amine (Compound 13): To a slurry of methylamine hydrochloride (1.7 g, 25.4 mmol) and sodium acetate (2.5 g, 30.48 mmol.) in methanol (20 mL) was added a solution of compound 2 (1.21 g, 5.08 mmol) in methanol (5 mL). The resulting mixture was treated with a solution of sodium cyanoborohydride (370 mg, 6.09 mmol) in methanol (5 mL) and heated to 80° C. After 1 h at 80° C., the reaction was cooled to room temperature and concentrated in vacuo. The residue was taken up into methylene chloride and 2N sodium hydroxide. The layers were separated and the organic phase washed with brine, dried over anhydrous magnesium sulfate, filtered and concentrated in vacuo to provide Compound 13.

Example 14

(S)-N-Methyl-2-(methyl-(2-oxo-2-(3,4,5-trimethoxyphenyl)acetyl)amino)-3 -phenyl-N-(3-(pyridin-4-yl)-1-(2-(pyridin-4-yl)-ethyl)propyl)propionamide (Compound 14): Compound 14 was prepared according to the protocols of Exanples 4–6, by replacing compound 3 with compound 13. $^1$H NMR as a mixture of rotomers (500 MHz, CDCl$_3$) δ 8.50–8.46 (m), 8.37 (d), 7.32–7.26 (m), 7.21–7.16(m), 7.10–7.06 (m), 6.97 (dd), 6.93 (d), 5.93 (d), 5.54 (t), 4.72 (br,s), 4.17 (m), 3.94 (s), 3.92 (s), 3.84 (s), 3.82 (s), 3.51 (dd), 3.38 (dd), 3.29 (s), 3.11 (dd), 3.06 (s), 3.00 (s), 2.97 (dd), 2.86 (s), 2.82 (s), 2.49 (m), 2.37–2.23 (m), 2.17–1.98 (m), 1.85–1.55 (m).

Example 15

(S)-N-Methyl-2-(methyl-(2-oxo-2-(3,4,5-trimethoxyphenyl)acetyl)amino)-3-phenyl-N-(3-(pyridin-4 -yl(acetyl)amino)-3-phenyl-N-(3-(pyridin-4-yl)-1-(2-(pyridin-4-yl)-propyl)butyl)propionamide (Compound 15): Compound 15 was prepared according to the protocols of Examples 13 and 14, by replacing compound 2 with compound 11. $^1$H NMR as a mixture of rotomers (500 MHz, CDCl$_3$) δ8.44–8.38 (m), 8.37–8.30 (m), 7.50–7.43 (m), 7.38–7.08 (m), 7.04 (s), 7.03–6.98 (m), 6.90–6.86 (m), 5.83 (dd), 5.74 (t) 4.75 (t), 4.65 (m), 3.94–3.93 (m), 3.92 (s), 3.90 (s), 3.84 (s), 3.83 (s), 3.44 (dd), 3.32 (dd), 3.20 (s), 3.01 (dd), 2.95 (s), 2.91 (s), 2.87 (dd), 2.59 (s), 2.58–2.37 (m), 1.68–1.00 (m).

Example 16

(S)-4-Methyl-2-(2-oxo-2-(3,4,5-trimethoxyphenyl)acetyl)amino)pentanoic acid benzyl (3-(pyridin-4-yl)-1-(2-(pyridin-4-yl)ethyl)propyl)amide (Compound 16): Compound 16 was prepared according to the protocols of Examples 3–6, by replacing 4-fluorobenzylamine with benzylamine and (L)-BOC-N-methylphenylalanine with (S)-BOC-N-methylleucine.

Example 17

(S)-4-Methyl-2-(methyl-2-oxo-2-(3,4,5-trimethoxyphenyl)acetyl)amino)pentanoic acid 4-fluorobenzyl (3-pyridin-4-yl1-(2-pyridin-4-yl-ethyl)propyl)amide (Compound 17): Compound 17 was prepared according to the protocols of Examples 4–6, by replacing (L)-Boc-N-methylphenylalamine with (S)-Boc-N-methylleucine. $^1$H NMR as a mixture of rotomers (500 MHz, CDCl$_3$) δ8.48 (m), 8.45 (d), 7.32 (m), 7.18 (s), 7.12 (s), 7.09–6.92 (m), 6.84 (d), 5.72 (dd), 5.48 (dd), 4.99 (br d), 4.68 (d), 4.42 (d), 4.36 (d), 4.29 (m), 3.94 (s), 3.91 (s), 3.87 (s), 3.83 (s), 2.96 (s), 2.92 (s), 2.69 (dr), 2.62–2.55 (m), 2.52–2.44 (m), 2.12–1.73 (m), 1.63–1.57 (m), 1.48–1.39 (m), 1.23 (m), 1.03 (t), 0.90 (d), 0.69 (d).

Example 18

(S)-4-Methyl-2-(methyl-(2-oxo-2-(3,4,5-trimethoxyphenyl)acetyl)amino)pentanoic acid 4-chlorobenzyl(3-pyridin-4-yl-1-(2-pyridin-4-yl-ethyl)propyl)amide (Compound 18): Compound 18 was prepared according to the protocols of Examples 3–6, by replacing 4-fluorobenzylamine with 4-chlorobenzylamine and (L)-Boc-N-methylphenylalanine with (S)-Boc-N-methylleucine. $^1$H NMR as a mixture of rotomers (500 MHz, CDCl$_3$) δ8.50 (m), 8.47 (d), 7.38 (d), 7.30–7.26 (m), 7.19 (s), 7.13 (s), 7.10 (d), 7.04 (d), 6.98 (d), 6.84 (d), 5.73 (dd), 5.47 (dd), 5.03 (br d), 4.69 (d), 4.42 (d), 4.36 (d), 4.31 (m), 3.95 (s), 3.93 (s), 3.88 (s), 3.84 (s), 2.97 (s), 2.94 (s), 2.70 (dr), 2.63–2.43 (m), 2.12–1.56 (m), 1.48–1.40 (m), 1.25 (m), 1.04 (t), 0.91 (d), 0.70 (d).

Example 19

(S)-N-(4-fluorobenzyl)-3-(4-chlorophenyl)-2-(methyl-2-oxo-2-(3,4,5 -triethoxyphenyl)acetyl)amino)-N-(3-pyridin-4-yl-1-(2-pyridin-4 -yl-ethyl)propyl)propionamide (Compound 19): Compound 19 was prepared according to the protocols of Examples 4–6, by replacing (L)-Boc-N-methylphenylalanine with (L)-Boc-N-methyl-4-chlorophenylalanine. $^1$H NMR as a mixture of rotomers (500 MHz, CDCl$_3$) δ8.49–8.41 (m), 7.34 (s), 7.28–7.20 (m), 7.10–6.90 (m), 6.64 (d), 5.92 (dd), 5.74 (t), 4.95 (br d), 4.74 (d), 4.24–4.13 (m), 3.94 (s), 3.90 (s), 3.86 (s), 3.77 (s), 3.54 (dd), 3.23–3.17 (m), 2.99 (s), 2.98 (s), 2.90 (d), 2.63 (dt), 2.59–2.37 (m), 2.28 (dt), 1.94–1.70 (m), 1.57–1.47 (m).

Example 20

(4-Chlorobenzyl)-(3-imidazol-1-yl-propyl)amine (Compound 20): To a solution of 1-(3-aminopropyl)imidazole 2.1 g, 16.8 mmol), diisopropylethylamine (3.5 mL, 20.0 mmol) and 4-N,N-dimethylaminopyridine (200 mg, 1.7 mmol) in methylene chloride (15 mL) at 0° C. was added dropwise 4-chlorobenzoylchloride (2.1 mL, 16.8 mmol). The reaction was then allowed to warm to room temperature. After 5 hours, the reaction was diluted with methylene chloride, washed with 1N sodium hydroxide, brine, dried over anhydrous magnesium sulfate, filtered and concentrated in vacuo to provide a white solid. This material was washed with diethyl ether to provide N-(3-imidazol-1-yl-propyl)-4-chlorobenzamide. To a slurry of the above amide (1.58 g, 6.0 mmol.) in tetrahydrofuran (30 mL) was slowly added lithium aluminum hydride (456 mg, 12.0 mmol) upon which the reaction became exothermic. The mixture was heated to 80° C., stirred for 1 hr, cooled to 0° C. and quenched by addition of water (0.5 mL), 15% sodium hydroxide (0.5 mL) and an additional 1.5 mL of water. The reaction was diluted with ethyl acetate, dried over anhydrous magnesium sulfate, filtered and concentrated in vacuo to provide compound 20.

Example 21

(S)-N-(4-chlorobenzyl)-N-(3-imidazol-1-yl-propyl)-2-(2-oxo-2-(3,4,5 -trimethoxyphenyl)acetyl)amino)-3-phenyl-propionamide (Compound 21): Compound 21 was prepared according to the protocols of Examples 4–6, by replacing compound 3 with compound 20. $^1$H NMR as a mixture of rotomers (500 MHz, CDCl$_3$) δ8.48 (m), 7.44 (br s), 7.37 (br s), 7.30–7.16 (m), 7.10–7.02 (m), 6.95 (d), 6.83 (m), 5.78 (t), 5.72 (t), 4.77 (d), 4.57 (d), 4.26 (dd), 3.94 (s), 3.93 (s), 3.88–3.77 (m), 3.80 (s), 3.48 (dr), 3.42–3.33 (m), 3.19–3.14 (m), 3.13 (s), 3.12 (s), 3.13–2.97 (m), 2.89 (t), 2.80 (m), 2.74 (t), 2.65 (m), 2.08–1.98 (m), 1.90 (m), 1.80–1.60 (m).

Example 22

N-(1H-Imidazol-2-yl-methyl)-N-(1-phenethyl-3-phenyl-propyl)amine (Compound 22): To a solution of 1,5-Diphenylpentan-3-one (5.26 g, 22.1 mmol), ammonium acetate (8.52 g, 110.5 mmol) and sodium acetate (9.06 g, 110.5 mmol) in methanol (80 mL) was added a solution of sodium cyanoborohydride (1.67 g, 26.52 mmol) in methanol (20 mL) and the reaction heated to reflux. After stirring at reflux for 30 min, the reaction was cooled and concentrated to dryness. The residue was partioned between methylene chloride and 2N sodium hydroxide. The organic phase was separated, washed with brine, dried over anhydrous magnesium sulfate, filtered and concentrated in vacuo. Chromatography of the residue on silica gel (elution with 2–5% methanol/methylene chloride) provided N-(1-phenethyl-3-phenyl-propyl)amine. To a solution of the above amine (2.1 g, 8.82 mmol) in ethanol (50 mL), was added 2-imidazolecarboxaldehyde (813 mg, 8.47 mmol) and the reaction heated to 50° C. After stirring for 2 hr, the resulting homogeneous solution was treated with sodium borohydride (400 mg, 10.58 mmol) and allowed to stir overnight. The reaction was concentrated to dryness and the residue was partioned between methylene chloride and 2N sodium hydroxide. The organic phase was separated, washed with brine, dried over anhydrous magnesium sulfate, filtered and concentrated in vacuo. Chromatography of the residue on silica gel (elution with 5% methanol/methylene chloride) provided compound 22.

Example 23

(S)-N-(1H-Imidazol-2-yl-methyl)-2-(methyl, (2-oxo-2-(3,4,5 -trimethoxyphenyl)acetyl)amino)-N-(1-phenethyl-3-phenyl-propyl)3-phenyl-propionamide (Compound 23): Compound 23 was prepared according to the protocols of Examples 4–6, by replacing compound 3 with compound 22. $^1$H NMR as a mixture of rotomers (500 MHz, CDCl$_3$) δ7.40–7.00 (m), 6.95–6.87 (m), 5.95 (t), 5.69 (t), 4.66 (d), 4.46 (d), 4.12 (m), 3.94 (s), 3.92 (s), 3.82 (s), 3.81 (s), 3.80 (s), 3.47 (s), 3.43 (dd), 3.34 (dd), 3.22 (s), 3.15 (s), 3.03 (dd), 3.00 (s), 2.60 (dt), 2.45–2.22 (m), 1.80–1.78 (m).

Example 24—MDR SENSITIZATION ASSAYS

To assay the ability of the compounds according to this invention to increase the antiproliferative activity of a drug, cell lines which are known to be resistant to a particular drug may be used. These cell lines include, but are not limited to, the L1210, P388D, CHO and MCF7 cell lines. Alternatively, resistant cell lines may be developed. The cell line is exposed to the drug to which it is resistant, or to the test compound; cell viability is then measured and compared to the viability of cells which are exposed to the drug in the presence of the test compound.

We have carried out assays using L1210 mouse leukemia cells transformed with the pHaMDR1/A retrovirus carrying a MDR1 cDNA, as described by Pastan et al., *Proc. Natl. Acad. Sci.*, Vol. 85, 4486–4490 (1988). The resistant line, labelled L1210VMDRC.06, was obtained from Dr. M. M. Gottesman of the National Cancer Institute. These drug-resistant transfectants had been selected by culturing cells in 0.06 mg/ml colchicine.

Multi-drug resistance assays were conducted by plating cells ($2\times10^3$, $1\times10^4$, or $5\times10^4$ cells/well) in 96 well microtiter plates and exposing them to a concentration range of doxorubicin (50 nM-10 µM) in the presence or absence of multi-drug resistance modifier compounds ("M/DR inhibitors") of this invention (1, 2.5 or 10 µM) as described in Ford et al., *Cancer Res.*, Vol. 50, 1748–1756. (1990). After culture for 3 days, the viability of cells was quantitated using MTT (Mossman) or XTT dyes to assess mitochondrial function. All determinations were made in replicates of 4 or 8. Also see, Mossman T., *J. Immunol. Methods*, Vol. 65, 55–63 (1983).

Results were determined by comparison of the $IC_{50}$ for doxorubicin alone to the $IC_{50}$ for doxorubicin+MDR inhibitor. An MDR ratio was calculated ($IC_{50}$ Dox/$IC_{50}$ Dox+Inhibitor) and the integer value used for comparison of compound potencies.

In all assays, compounds according to this invention were tested for intrinsic antiproliferative or cytotoxic activity. The results are summarized in Table 2 below. As demonstrated in Table 2, the compounds generally caused <10% cytotoxicity at concentrations of 10 µM or greater. In Table 2, "NT" indicates that the compound was not tested at the respective concentration.

TABLE 2

Evaluation of Compounds for Reversal of MDR

| Compound | $IC_{50}$ Dox Alone | $IC_{50}$ Dox + .5 µM Cpd. | $IC_{50}$ Dox + 1.0 µM Cpd. | MDR Ratio 0.5 µM | MDR Ratio 1.0 µM |
|---|---|---|---|---|---|
| 6 | 350 | 65 | <50 | 5.4 | >7.0 |
| 7 | 425 | 95 | <50 | 4.5 | >8.5 |
| 8 | 600 | 55 | 150 | 4.0 | 10.9 |
| 9 | 275 | <50 | <50 | >5.5 | >5.5 |
| 10 | 400 | 170 | 65 | 2.4 | 6.1 |
| 12 | 460 | 125 | <50 | 3.2 | >9.2 |
| 14 | 775 | 610 | 350 | 1.3 | 2.2 |
| 15 | 375 | 375 | 175 | 1.0 | 2.1 |
| 16 | 350 | 65 | <50 | 5.4 | >7.0 |
| 21 | 350 | 275 | 85 | 1.3 | 4.1 |
| 23 | 600 | 125 | <50 | 4.8 | >12.0 |
| CsA | 500 | NT | <55 | NT | >9.1 |

Example 25

Inhibition of MRP-Mediated MDR

In order to demonstrate that the compounds of this invention are effective in reversing MPR-mediated MDR, in addition to P-glycoprotein-mediated MDR, we assayed inhibition in a non-P-glycoprotein expressing cell line.

We plated HL60/ADR cells in 96 well microtiter plates ($4\times10^4$ cells/well). The cells were then exposed to various concentrations of doxorubicin (50 nM to 10 µM) in the presence or absence of various compounds of this invention at various concentrations (0.5–10 µM). After culturing the cells for 3 days, their viability was quantitated using the XTT dye method to assess mitochondrial function. Results were expressed as a ratio of the $IC_{50}$ for doxorubicin alone to the the $IC_{50}$ for doxorubicin plus MDR inhibitor. $IC_{50}$ values are expressed in nM. In all assays the intrinsic antiproliferative or cytotoxicity activity of the MDR inhibitors was also determined for HL60/ADR cells. The results of this assay are set forth in Table 3 below:

TABLE 3

Reversal Of MRP-meidated MDR in HL60/ADR Cells

| Cmpd | $IC_{50}$ Dox alone | $IC_{50}$ Dox + 0.5 µM Cpd | $IC_{50}$ Dox + 1 µM Cpd | $IC_{50}$ Dox + 2.5 µM Cpd | $IC_{50}$ Dox + 5 µM Cpd | $IC_{50}$ Dox + 10 µM Cpd | MDR Ratio 0.5 µM | MDR Ratio 1 µM | MDR Ratio 2.5 µM | MDR Ratio 5 µM | MDR Ratio 10 µM |
|---|---|---|---|---|---|---|---|---|---|---|---|
| 7 | 5 | 1.8 | 1.1 | 0.625 | 0.4 | 0.08 | 4.4 | 4.5 | 8 | 12.5 | 62.5 |
| 8 | 5 | 1.1 | 0.8 | 0.5 | 0.4 | 0.2 | 4.5 | 6.3 | 10 | 12.5 | 25 |
| 9 | 5 | 1 | 0.6 | 0.2 | 0.2 | 0.04 | 5 | 8.3 | 25 | 25 | 125 |

While we have described a number of embodiments of this invention, it is apparent that our basic constructions may be altered to provide other embodiments which utilize the products, processes and methods of this invention. Therefore, it will be appreciated that the scope of this invention is to be defined by the appended claims, rather than by the specific embodiments which have been presented by way of example.

I claim:

1. A compound of formula (I):

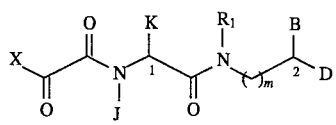

wherein:

R₁, B and D are independently:

hydrogen, Ar, (C1–C6)-straight or branched alkyl, (C2–C6)-straight or branched alkenyl or alkynyl, (C5–C7)-cycloalkyl substituted (C1–C6)-straight or branched alkyl, (C5–C7)-cycloalkyl substituted (C3–C6)-straight or branched alkenyl or alkynyl, (C5–C7)-cycloalkenyl substituted (C1–C6)-straight or branched alkyl, (C5–C7)-cycloalkenyl substituted (C3–C6)-straight or branched alkenyl or alkynyl, Ar-substituted (C1–C6)-straight or branched alkyl, Ar-substituted (C3–C6)-straight or branched alkenyl or alkynyl; provided that R₁ is not hydrogen;

wherein any one of the CH₂ groups of said alkyl chains is optionally replaced by a heteroatom selected from the group consisting of O, S, SO, SO₂, and NR; wherein R is selected from the group consisting of hydrogen, (C1–C4)-straight or branched alkyl, (C3–C4)-straight or branched alkenyl or alkynyl, and (C1–C4) bridging alkyl wherein a bridge is formed between the nitrogen and a carbon atom of said heteroatom-containing chain to form a ring, and wherein said ring is optionally fused to an Ar group;

J is selected from the group consisting of (C1–C6)-straight or branched alkyl, (C3–C6)-straight or branched alkenyl, Ar-substituted (C1–C6)-straight or branched alkyl, and Ar-substituted (C3–C6)-straight or branched alkenyl or alkynyl;

K is selected from the group consisting of (C1–C6)-straight or branched alkyl, Ar-substituted (C1–C6)-straight or branched alkyl, Ar-substituted (C2–C6)-straight or branched alkenyl or alkynyl, and cyclohexylmethyl;

X is selected from the group consisting of Ar, —OR₂, and —NR₃R₄;

wherein R₂ has the same definition as R₁; and R₃ and R₄ independently have the same definitions as B and D; or R₃ and R₄ are taken together to form a 5–7 membered heterocyclic aliphatic or aromatic ring;

wherein Ar is a carbocyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar is optionally substituted with one or more substituents which are independently selected from the group consisting of hydrogen, halogen, hydroxyl, nitro, —SO₃H, trifluoromethyl, trifluoromethoxy, (C1–C6)-straight or branched alkyl, (C2–C6)-straight or branched alkenyl, O-[(C1–C6)-straight or branched alkyl], O-[(C3–C4)-straight or branched alkenyl], O—benzyl, O—phenyl, 1,2-methylenedioxy, —NR₅R₆, carboxyl, N-(C1–C5-straight or branched alkyl or C3–C5-straight or branched alkenyl) carboxamides, N,N-di-(C1–C5-straight or branched alkyl or C3–C5-straight or branched alkenyl) carboxamides, morpholinyl, piperidinyl, O—M, CH₂—(CH₂)_q—M, O—(CH₂)_q—M, (CH₂)_q—O—M, and CH=CH—M;

wherein R₅ and R₆ are independently selected from the group consisting of hydrogen, (C1–C6)-straight or branched alkyl, (C3–C6)-straight or branched alkenyl or alkynyl and benzyl;

wherein M is selected from the group consisting of 4-methoxyphenyl, 2-pyridyl, 3-pyridyl, 4-pyridyl, pyrazyl, quinolyl, 3,5-dimethylisoxazoyl, 2-methylthiazoyl, thiazoyl, 2-thienyl, 3-thienyl and pyrimidyl; and q is 0–2; and m is 0 or 1.

2. The compound of formula (I) according to claim 1, wherein at least one of B or D is independently represented by the formula —(CH₂)_r—(Z)—CH₂)_s—Ar, wherein:

r is 1–4;

s is 0–1;

Ar is as defined in claim 1; and each Z is independently selected from the group consisting of CH₂, O, S, SO, SO₂, and NR, wherein R is selected from the group consisting of hydrogen, (C1–C4)-straight or branched alkyl, (C3–C4)-straight or branched alkenyl or alkynyl, and (C1–C4) bridging alkyl, wherein a bridge is formed between the nitrogen atom and the Ar group.

3. The compound of formula (I) according to claim 1 or 2, wherein Ar is selected from the group consisting of phenyl, 2-pyridyl, 3-pyridyl, 4-pyridyl, imidazolyl, indolyl, isoindolyl, quinolinyl, isoquinolinyl, 1,2,3,4-tetrahydroisoquinolinyl, and 1,2,3,4-tetrahydroquinolinyl, wherein said Ar may contain one or more substituents which are independently selected from the group consisting of hydrogen, hydroxyl, nitro, trifluoromethyl, (C1–C6)-straight or branched alkyl, O-[(C1–C6)-straight or branched alkyl], halogen, SO₃H, and NR₃R₄, wherein R₃ and R₄ are independently selected from the group consisting of (C1–C6)-straight or branched alkyl, (C3–C6)-straight or branched alkenyl, hydrogen and benzyl; or wherein R₃ and R₄ can be taken together to form a 5–6 membered heterocyclic ring.

4. A compound of formula (II) or (III):

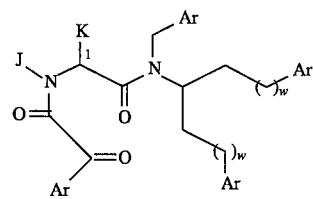

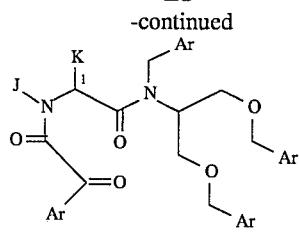

wherein J and K are independently (C1–C6)-straight or branched alkyl or Ar-substituted (C1–C6)-straight or branched alkyl;

each Ar is independently as defined in claim 3 and each w is 1 or 2.

5. A compound selected from compound 6, compound 7, compound 8, compound 9, compound 10, compound 12, compound 14, compound 15, compound 16, compound 17, compound 18, compound 19, compound 21 or compound 23 as defined in Table 1.

6. A compound selected from the group consisting of:
- (S)-N-(4-Fluorobenzyl)-2-(methyl-(2-oxo-2-(3,4,5-trimethoxyphenyl)acetyl)amino)-3-phenyl-N-(3-(pyridin-4-yl)-1-(2-(pyridin-4-yl)-ethyl)propyl)propionamide (compound 6);
- (S)-N-(4-Chlorobenzyl)-2-(methyl-(2-oxo-2-(3,4,5-trimethoxyphenyl)acetyl)amino)-3-phenyl-N-(3-(pyridin-4-yl)-1-(2-(pyridin-4-yl)-ethyl)propyl)propionamide (compound 8);
- (S)-N-Benzyl-3-(4-chlorophenyl)-2-(methyl-(2-oxo-2-(3,4,5-trimethoxyphenyl)acetyl)amino)-N-(3-(pyridin-4-yl)-1-(2-(pyridin-4-yl)-ethyl)propyl)propionamide (compound 9); and
- (S)-N-4-fluorobenzyl-3-(4-chlorophenyl)-2-(methyl-(2-oxo-2-(3,4,5-trimethoxyphenyl)acetyl)amino)-N-(3-pyridin-4-yl-1-(2-pyridin-4-yl-ethyl)propyl)propionamide (compound 19).

7. A compound of formula (XXXI):

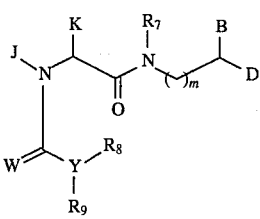

wherein:

m, B, D, J, K and Ar are as defined in claim 1;

$R_7$ is Ar, (C1–C6)-straight or branched alkyl, (C2–C6)-straight or branched alkenyl or alkynyl, (C5–C7)-cycloalkyl-substituted (C1–C6)-straight or branched alkyl, (C5–C7)-cycloalkyl-substituted (C3–C6)-straight or branched alkenyl or alkynyl, (C5–C7)-cycloalkenyl-substituted (C1–C6)-straight or branched alkyl, (C5–C7)-cycloalkenyl-substituted (C3–C6)-straight or branched alkenyl or alkynyl, Ar-substituted (C1–C6)-straight or branched alkyl, Ar-substituted (C3–C6)-straight or branched alkenyl or alkynyl;

wherein any one of the $CH_2$ groups of said alkyl chains is optionally replaced by a heteroatom selected from the group consisting of O, S, SO, $SO_2$, and NR; wherein R is selected from the group consisting of hydrogen, (C1–C4)-straight or branched alkyl, (C3–C4)-straight or branched alkenyl or alkynyl, and (C1–C4) bridging alkyl wherein a bridge is formed between the nitrogen and a carbon atom of said heteroatom-containing chain to form a ring, and wherein said ring is optionally fused to an Ar group;

W is O or S;

Y is O or N, provided that when Y is O, then:
- $R_8$ is a lone pair (as used herein, the term "lone pair" refers to a lone pair of electrons, such as the lone pair of electrons present on divalent oxygen); and
- $R_9$ is selected from the group consisting of Ar, (C1–C6)-straight or branched alkyl, and (C3–C6)-straight or branched alkenyl or alkynyl; and when Y is N, then:
- $R_8$ and $R_9$ are independently selected from the group consisting of Ar, (C1–C6)-straight or branched alkyl, and (C3–C6)-straight or branched alkenyl or alkynyl; or $R_8$ and $R_9$ are taken together to form a heterocyclic 5–6 membered ring selected from the group consisting of pyrrolidine, imidazolidine, pyrazolidine, piperidine, and piperazine.

8. The compound of formula (XXXI) according to claim 7, wherein W is oxygen.

9. The compound of formula (XXXI) according to claim 7 or claim 8, wherein at least one of B or D is independently represented by the formula $-(CH_2)_r-(Z)-(CH_2)_s-Ar$, wherein:

r is 1–4;

s is 0–1;

Ar is as defined in claim 1; and each Z is independently selected from the group consisting of $CH_2$, O, S, SO, $SO_2$, and NR, wherein R is selected from the group consisting of hydrogen, (C1–C4)-straight or branched alkyl, (C3–C4)-straight or branched alkenyl or alkynyl, and (C1–C4) bridging alkyl, wherein a bridge is formed between the nitrogen atom and the Ar group.

10. A pharmaceutical composition for treatment or prevention of multi-drug resistance, comprising:

a) a compound according to any one of claims 1–7, in an amount effective to prevent, maintains increase or restore drug sensitivity in multi-drug resistance cells; and b) a pharmaceutically acceptable carrier, adjuvant or vehicle.

11. The pharmaceutical composition according to claim 10, further comprising a chemotherapeutic agent.

12. The pharmaceutical composition according to claim 10 or 11, further comprising a chemosensitizer, other than the compound according to any one of claims 1–7.

13. A method for treating or preventing multi-drug resistance in a patient, comprising the step of administering to said patient a pharmaceutical composition according to claim 10.

14. The method according to claim 13, wherein said composition is administered orally.

15. The method according to claim 13 or 14, wherein said multi-drug resistance is P-glycoprotein-mediated.

16. The method according to claim 13 or 14, wherein said multi-drug resistance is MRP-mediated.

17. A process for the synthesis of a compound of formula (I), according to any one of claims 2 to 3, or 1 comprising the steps of:

(a) coupling an amino acid of formula (IV) with an amine of formula (V):

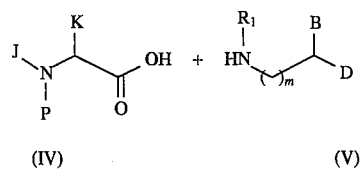
(IV)   (V)
to give an amino amide of formula (VI):
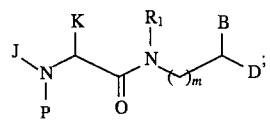
(VI)
(b) deprotecting the amide of formula (VI) to give an amino amide of formula (VII):
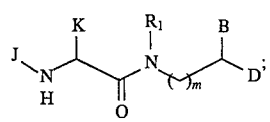
(VII)
(c) acylating the amino amide of formula (VII) with compound of formula (VIII):
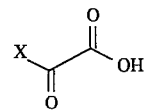
(VIII)
wherein B, D, J, K, X and $R_1$ are as defined in claim 1.
* * * * *

UNITED STATES PATENT AND TRADEMARK OFFICE
CERTIFICATE OF CORRECTION

PATENT NO. : 5,543,423
DATED : August 6, 1996
INVENTOR(S) : Robert E. Zelle, et al.

It is certified that error appears in the above-identified patent and that said Letters Patent is hereby corrected as shown below:

Column 1,
Line 46, delete "P-glycoprtoein" and substitute therefor -- P-glycoprotein --.
Line 47, delete "brast" and substitute therefor -- breast --.

Column 4,
Line 2, delete "$(CH_{2q}$" and substitute therefor -- $(CH_2)_q$ --.

Column 9, scheme 5,
Line 23, delete "(IV)" and substitute therefor -- (I'V) --.

Column 10, and Column 20,
Line 11, and Table 3, delete "meidated" and substitute therefor -- mediated --.

Column 13,
Line 9, delete "Me4Si" and substitute therefor -- $Me_4Si$ --.
Line 28, delete "form" and substitute therefor -- from --.
Line 48, delete "(pyridin-4-y)" and substitute therefor -- (pyridin-4-yl) --.

Column 16,
Line 17, delete "2.2" and substitute therefor -- 2.22 --.
Line 23, after "(pyridin-4-yl)-1-" insert -- (2- --.
Line 57, delete "(acety-".
Line 58, delete "1)amino)-3-phenyl-N-(3-pyridin-4-yl)."

Column 17,
Line 2, after "Methyl-2" insert -- methyl- --.
Lines 22 and 39, delete "(dr)" and substitute therefor -- (dt) --.
Line 43, delete "2-(methyl-2-" and substitute therefor -- 2-(methyl-(2- --.
Line 44, delete "(3,4,5-triethoxyphenyl)" and substitute therefor -- (3,4,5-trimethoxyphenyl) --.

Column 18,
Line 14, delete "2-(2-" and substitute therefor -- 2-(methyl-(2- --.
Line 58, delete "2-(methyl, (2-oxo-2-)" and substitute therefor -- 2-(methyl-(2-oxo-2-) --.

UNITED STATES PATENT AND TRADEMARK OFFICE
CERTIFICATE OF CORRECTION

PATENT NO. : 5,543,423
DATED : August 6, 1996
INVENTOR(S) : Robert E. Zelle, et al.

It is certified that error appears in the above-identified patent and that said Letters Patent is hereby corrected as shown below:

Column 19,
Line 24, delete "M/DR" and substitute therefor -- MDR --.

Column 22,
Line 30, delete "(Z)-CH$_2$)$_s$" and substitute therefor -- (Z)-(CH$_2$)$_s$ --.

Column 24,
Line 41, delete "maintains" and substitute therefor -- maintain, --.
Lines 40 and 50, delete "1-7" and substitute therefor -- 1-9 --.
Line 63, delete "2 to 3, or, 1" and substitute therefor -- 1-3 --.

Signed and Sealed this

Sixth Day of November, 2001

Attest:

NICHOLAS P. GODICI
Attesting Officer
Acting Director of the United States Patent and Trademark Office